(12) United States Patent
Nguyen et al.

(10) Patent No.: US 11,596,397 B2
(45) Date of Patent: Mar. 7, 2023

(54) MICRONEEDLE, MOLD FOR PRODUCTION OF MICRONEEDLE ARRAY, AND PRODUCTION METHOD OF MICRONEEDLE ARRAY USING SAME

(71) Applicant: Fdn. for Res. & Bus., Seoul Nat. Univ. of Sci. & Tech., Seoul (KR)

(72) Inventors: Thanh-Qua Nguyen, Seoul (KR); Le Giang Tran, Seoul (KR); Woo-Tae Park, Seoul (KR)

(73) Assignee: Foundation for Research and Business, Seoul National University of Science and Technology, Seoul (KR)

( * ) Notice: Subject to any disclaimer, the term of this patent is extended or adjusted under 35 U.S.C. 154(b) by 656 days.

(21) Appl. No.: 16/681,081

(22) Filed: Nov. 12, 2019

(65) Prior Publication Data

US 2021/0059660 A1 Mar. 4, 2021

(30) Foreign Application Priority Data

Aug. 29, 2019 (KR) .......... 10-2019-0106461

(51) Int. Cl.
*A61B 17/064* (2006.01)
*B29C 33/38* (2006.01)
(Continued)

(52) U.S. Cl.
CPC ........ *A61B 17/064* (2013.01); *B29C 33/3842* (2013.01); *B29C 39/026* (2013.01);
(Continued)

(58) Field of Classification Search
CPC ........ A61B 17/064; A61B 2017/00526; A61B 2017/0647; A61B 2017/0641;
(Continued)

(56) References Cited

FOREIGN PATENT DOCUMENTS

| KR | 10-1634911 B1 | 6/2016 |
|----|---------------|--------|
| KR | 10-1878414    | 7/2018 |

OTHER PUBLICATIONS

Nguyen, Thanh Qua, and Woo-Tae Park. "Rapid, low-cost fabrication of circular microchannels by air expansion into partially cured polymer." Sensors and Actuators B: Chemical 235 (2016): 302-308. (Year: 2016).*

(Continued)

*Primary Examiner* — Leith S Shafi
(74) *Attorney, Agent, or Firm* — HoustonHogle LLP

(57) ABSTRACT

The present invention includes producing a preliminary mold (10-1 or 20-1) provided with two-dimensional patterns (111 or 211) having a shape of a microneedle array (30) therein; producing microneedle array molds (10 and 10-2 or 20 and 20-2) having a three-dimensional shape by expanding air inside the patterns (111 or 211) having a two-dimensional shape to deform the patterns (111 or 211) having the two-dimensional shape into molds having the three-dimensional shape; and after pouring a biodegradable resin into the microneedle array molds (10 and 10-2 or 20 and 20-2) and solidifying the biodegradable resin, completing the microneedle array (30) by removing the microneedle array molds (10 and 10-2 or 20 and 20-2), thereby providing a mold for production of a microneedle array and a production method of the microneedle array using the same capable of tightly suturing an affected area without inducing pain.

11 Claims, 10 Drawing Sheets

(51) Int. Cl.
*B29C 39/26* (2006.01)
*B33Y 80/00* (2015.01)
*B29C 39/02* (2006.01)
B29L 31/00 (2006.01)
A61B 17/00 (2006.01)

(52) U.S. Cl.
CPC .............. *B29C 39/26* (2013.01); *B33Y 80/00* (2014.12); *A61B 2017/00526* (2013.01); *A61B 2017/0647* (2013.01); *B29L 2031/7544* (2013.01)

(58) Field of Classification Search
CPC ......... A61B 17/04; A61B 17/08; A61B 5/685; B29C 33/3842; B29C 39/026; B29C 39/26; B29C 33/3857; B29C 33/40; B29C 33/42; B33Y 80/00; B29L 2031/7544; B29L 2031/756; A61F 13/00021; A61F 2013/00451; A61M 37/0015; A61M 2037/0053; A61K 9/70

See application file for complete search history.

(56) References Cited

OTHER PUBLICATIONS

Nguyen, Thanh-Qua, and Woo-Tae Park. "Rapid, low cost fabrication of circular cross-section microchannels by thermal air molding." 2015 28th IEEE International Conference on Micro Electro Mechanical Systems (MEMS). IEEE, 2015. (Year: 2015).*
Tran, Le-Giang, Thanh-Qua Nguyen, and Woo-Tae Park. "Bio-inspired barbed microneedle for skin adhesion with interlocking mechanics." 2019 IEEE 32nd International Conference on Micro Electro Mechanical Systems (MEMS). IEEE, 2019. (Year: 2019).*

* cited by examiner

Table: Comparison of the bio-inspired barbed microneedle with state-of-the-art interlocking microneedles

| References | [1] | [2] | [3] | This work |
|---|---|---|---|---|
| Microneedle geometry | Barbed | Conical | Honey bee stinger | Barbed |
| Height (μm) | 2000 | 700 | ~1500 | 1300 |
| Base width (μm) | ~ 200 | 280 | ~100 | 380 |
| Retraction force (mN) | 73 | 93 | 141.5 | 107 |
| Materials | Curable magneto-rheological fluid | Ps-b-PAA | Stinger taken from the honey bee | Silk fibroin |

FIG. 8

MICRONEEDLE, MOLD FOR PRODUCTION OF MICRONEEDLE ARRAY, AND PRODUCTION METHOD OF MICRONEEDLE ARRAY USING SAME

CROSS REFERENCE TO RELATED APPLICATION

The present application claims priority to Korean Patent Application No. 10-2019-0106461, filed Aug. 29, 2019, the entire contents of which is incorporated herein for all purposes by this reference.

BACKGROUND OF THE INVENTION

Field of the Invention

The present invention relates to a production method of a microneedle array and a mold for production of a microneedle array, wherein the microneedle array is inserted into the skin for bioconjugation.

Description of the Related Art

When an incision occurs outside or inside a body, it should be sutured. However, human tissues and muscle fibers are accompanied by a problem of pain when physical means is used in a suturing process. In addition, difficult tasks remain after treatment of an affected part due to problems such as residual suturing material, scarring, additional bleeding, nerve damage, and the like.

Recently, in order not to leave suture marks or because of a case where bits of thread inside the human body are difficult to remove, medical adhesives are widely used to suture the wounds or surgical parts of human skin, muscle tissue, organs, and the like.

However, medical adhesives use chemicals, thereby inducing a problem of causing inflammation. Therefore, medical adhesives are difficult to settle as a safe alternative to a physical suture using a conventional thread.

In many medical practices such as surgeries for physical trauma or medical treatment, suturing is frequently performing. Therefore, a development of a technique, which can realize tight suturing of the affected part without inducing pain and to allow the human tissues to be sutured without having any residual side effects or problems such as the need to remove bits of thread inside the human body after suturing, remains as a big problem in the medical field. Accordingly, the development of the technique is a task that needs to be urgently solved.

The foregoing is intended merely to aid in the understanding of the background of the present invention, and is not intended to mean that the present invention falls within the purview of the related art that is already known to those skilled in the art.

DOCUMENTS OF RELATED ART

Patent Document (Patent Document 1) Korean Patent No. 10-1878414 (Publication date: Jul. 13, 2018)

SUMMARY OF THE INVENTION

Accordingly, the present invention has been made keeping in mind the above problems occurring in the related art, and the present invention is intended to propose a microneedle, a mold for production of a microneedle array, and a production method of the microneedle array, the microneedle being able to realize tight suturing of the affected part without inducing pain and to allow human tissues to be sutured without having any residual side effects or problems such as the need to remove bits of thread inside the human body after suturing.

The microneedle 1 according to the present invention in order to achieve the above objective, the microneedle including: a body made of biodegradable or biocompatible material, having a long length, and having one end formed pointed; and side surface wedges, as protrusions provided on the periphery of the body, each having an end part provided in an acute angle and in a shape inclined to an opposite end side of the body.

At this time, the protrusion may be provided along the outer circumferential surface of the body, and a plurality of protrusions configurates layers along the longitudinal direction of the body.

In addition, A production method of a microneedle array 30 according to the present invention, the microneedle array 30 composed of a base 31 and a plurality of microneedles 1 arranged on a surface of the base 31, the microneedle including a long needle-shaped body protruded from the base 31 and barb or wedge shapes each provided in an acute angle toward the base 31 along a circumference of the body, the method including: producing a preliminary mold 10-1 or 20-1 provided with two-dimensional patterns 111 or 211 having a shape of the microneedle array 30 therein; producing microneedle array molds 10 and 10-2 or 20 and 20-2 having a three-dimensional shape by expanding air inside the patterns 111 or 211 having a two-dimensional shape to deform the patterns 111 or 211 having the two-dimensional shape into a cast form having the three-dimensional shape; and after pouring a biodegradable resin into the microneedle array molds 10 and 10-2 or 20 and 20-2 and solidifying the biodegradable resin, completing the microneedle array 30 by removing the microneedle array molds 10 and 10-2 or 20 and 20-2.

At this time, in the producing the preliminary mold 10-1 or 20-1, the patterns 111 or 211 having the two-dimensional shape may be produced to have a predetermined thickness, thereby allowing the air to be contained inside the patterns 111 or 211 having the two-dimensional shape; and in the producing the microneedle array molds 10 and 10-2 or 20 and 20-2, the air inside the patterns 111 or 211 having the two-dimensional shape may expand as the preliminary mold 10-1 or 20-1 is heated, thereby allowing the two-dimensional patterns 111 or 211 to be deformed into the three-dimensional shape.

In addition, the producing the preliminary mold 10-1 or 20-1 may further include: preparing a first plate member 11 or 21 providing the microneedle patterns 111 or 211 having the two-dimensional shape having a predetermined depth on one surface of the first plate member 11 or 21; preparing a second plate member 12 or 22; and completing the preliminary mold 10-1 or 20-1 by bonding the first plate member 11 or 21 and the second plate member 12 or 22 to each other.

For all of the above-described cases, in the producing the preliminary mold 10-1 or 20-1, the first plate member 11 or 21 may allow the microneedle patterns 111 or 211 having the two-dimensional shape to be provided and then cured, and the second plate member 12 or 22 may allow a remaining portion except for a portion in contact with the microneedle patterns 111 or 211 to be cured, whereby a certain amount of the air is allowed to exist in the microneedle patterns 111 or 211 in contact with the bonding surface between the first plate member 11 or 21 and the second plate member 12 or 22; and in the producing the microneedle array molds 10 and 10-2 or 20 and 20-2, when the preliminary mold 10-1 or 20-1 is heated, the air existing in the microneedle patterns 111 or 211 may expand toward the second plate member 12 or 22, whereby a hollow space having a three-dimensional shape is allowed to be provided.

In this case, the producing the preliminary molds 10-1 and 20-1 may further include preparing a master mold providing the microneedle patterns 111 or 211 having the two-dimensional shape in the master mold by preparing the master mold prior to the preparing the first plate member 11 or 21, wherein, in the preparing the first plate members 11 or 21, the microneedle patterns 111 or 211 having the two-dimensional shape are provided on the first plate member 11 or 21 in a manner of replicating the master mold. The pattern 111 or 211 may be obtained through a process such as photolithography but may also be obtained through a process such as etching or stamping, and it is irrelevant as long as precision may be obtained.

At this time, substrate of the master mold (not shown) may be made of silicon material, and in the preparing the master mold, the microneedle patterns 111 or 211 having the two-dimensional shape may be provided on the prepared master mold by a photolithography process.

In addition, in the producing the preliminary mold 10-1 or 20-1, any one of microneedle arrays 30 may be arranged in a form, in which microneedles 1 are each arranged in one line and each have longitudinal directions all facing the same direction, and a plurality of microneedle arrays 30 is provided, wherein the plurality of microneedle arrays 30 is arranged in parallel with each other; and the producing the microneedle array molds 10 and 10-2 or 20 and 20-2 may further include, after the hollow space having the three-dimensional shape of the microneedle 1 is provided as the preliminary mold 10-1 or 20-1 is heated, opening the end portions of the microneedles 1 by cutting an end region of the base 31 side of the microneedles 1, arranged in one line for each microneedle array 30, along the virtual surface SF simultaneously passing through the end region of the base 31 side of the microneedles 1, and completing the microneedle array mold in which a plurality of microneedle arrays 30 is arranged in parallel with each other, by gathering all blocks of the microneedle array molds 10 and 10-2 or 20 and 20-2 provided by being cut along the virtual surface SF and then bonding the blocks to be in parallel with each other in a state where open end portions of all of the microneedles 1 face upward.

On the other hand, a mold for production of a microneedle array 30, the microneedle array 30 implemented by allowing microneedles to be arranged in one line and each one end thereof to be connected to a base member 31, the microneedle including a body having a long length in a needle-shape having a peak at an opposite end and a barb or wedge shape provided in an acute angle toward the one end of the body on a circumference of the body, the mold including: a first plate member 12 or 22 engraved with patterns 111 or 211 having a shape of the microneedle array 30, on one surface thereof; and a second plate member bonded with the one surface of the first plate member 12 or 22, wherein the second plate member 12 or 22 or the first plate member 11 or 21 is made of a member that may be plastically deformed, so that when air expands in the patterns 111 or 211, the two-dimensional patterns 111 or 211 are deformed into the three-dimensional shapes, whereby a hollow space having the shape of the microneedle array 30 is provided.

At this time, the first plate member 11 or 21 may be a member cured in a state of having the patterns 111 or 211 engraved on the one surface thereof, and on a surface of the second plate member 12 or 22 bonded to the first plate 11 or 21, a portion in contact with the patterns 111 or 211 is in a thermoplastic state and a remaining portion is in a cured state, whereby, when heat is applied in a state where the first plate member 11 or 21 and the second plate member 12 or 22 are bonded to each other, the second plate member 12 or 22 locally expands into a semicircular cross section shape from the portion in contact with the patterns 111 or 211 engraved on the first plate member 11 or 21, whereby a microneedle 1 shape is provided. For example, when using a thermosetting resin such as PDMS, the second plate member 12 may be possible to expand only when resin formed has a viscosity to some extent but is maintained in a state before being completely cured.

Accordingly, the microneedle according to the present invention has effects, one of which is that the affected part can be tightly sutured without pain, and another one of which is that the suture of the human tissues can be realized without leaving any side effects or problems such as the removal of bits of thread inside the human body after the suture. In addition, the mold for production of the microneedle array and the production method of the microneedle array according to the present invention have an effect that the microneedle, despite having a three-dimensional unique shape, can be produced inexpensively with a minimum process.

Accordingly, the microneedle according to the present invention has the following effects: the affected part can be tightly sutured without pain, and the suturing of human tissues can be realized without having any residual side effects or problems such as the need to remove bits of thread inside the human body after suturing. In addition, the mold for production of the microneedle array and the production method of the microneedle array according to the present invention have an effect that the microneedle, despite having a three-dimensional unique shape, can be produced inexpensively with a simple process.

BRIEF DESCRIPTION OF THE DRAWINGS

The above and other objectives, features, and other advantages of the present invention will be more clearly understood from the following detailed description when taken in conjunction with the accompanying drawings, in which:

FIG. 8 is a table showing performance test results according to FIG. 7; and

DETAILED DESCRIPTION OF THE INVENTION

Figure 1:
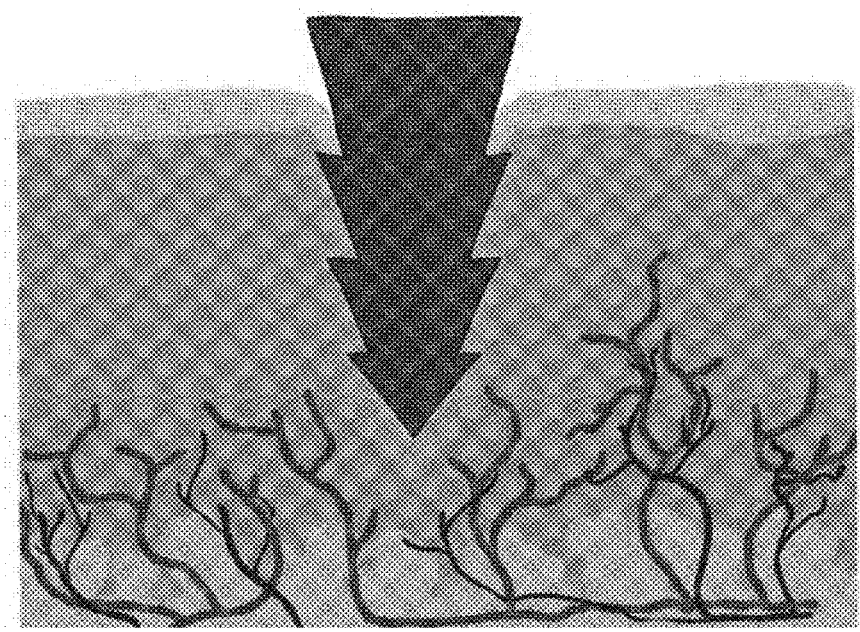
FIG. 1 is conceptual view showing a principle of a microneedle according to the present invention.

Specific structural or functional descriptions presented in embodiments of the present invention are illustrated only for the purpose of describing the embodiments according to a concept of the present invention, and the embodiments according to the concept of the present invention may be implemented in various forms. In addition, the present invention should not be construed as limited to the embodiments described herein and should be understood to include all modifications, equivalents, and substitutes included in the spirit and technical scope of the present invention.

Hereinbelow, the present invention will be described in detail with reference to the accompanying drawings. Throughout the drawings, the same reference numerals will refer to the same or like parts.

Hereinafter, the microneedle array 30 according to the present invention will be described first, and then, a mold for production of the microneedle array will be described together with describing the production method of the microneedle array.

A microneedle 1 according to the present invention includes a body and side surface wedges provided on the periphery of the body as shown in FIG. 1.

The body is made of biodegradable or biocompatible material, having a long length, and having one end formed pointed. Therefore, the one end is easily inserted into biological tissues when penetrating into the biological tissues for conjugation of the biological tissues.

The side surface wedges are protrusions provided on the periphery of the body as shown in FIG. 1, each having an end part provided in an acute angle and in a shape inclined to an opposite end side of the body.

Figure 2:
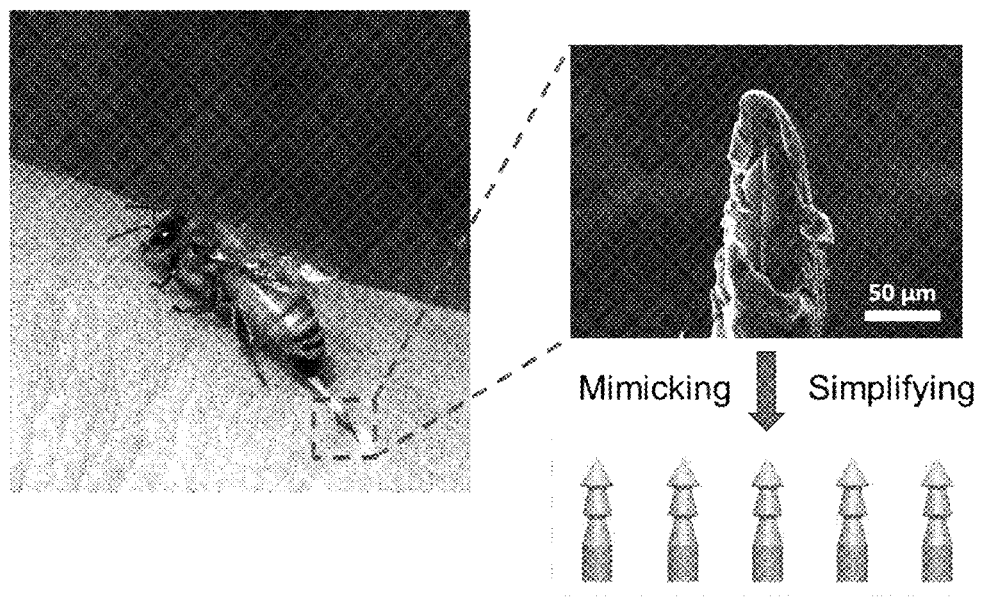
FIG. 2 shows conceptual views illustrating a biomimetic principle of the microneedle of FIG. 1.

The side surface wedges, as the name implies, are constructions devised inspired by a shape of a bee's stinger as shown in FIG. 2.

In order to perform bioconjugation by physical means, the pain and bleeding should be minimized, and while the conjugation should be tight, no post-treatment such as removal of the conjugation means should not be required. In order for these seemingly contradictory requirements to be realized by one means, first, the means is made of biodegradable or bioconjugated material in order not to require post-processing, such as removal of the joining means.

Next, minimization of "bleeding and pain" and tightness of the conjugation should be satisfied at the same time. However, the above-mentioned two requirements are difficult to satisfy at the same time. That is, when subminiature pieces of needle material for conjugation are produced in order to minimize bleeding and pain, the pain and damage to the human body may be minimized in a process of insertion into the human body, but conjugation strength is weak and the needle material may be easily separated from the human body.

Therefore, in order to solve such a problem, the microneedle 1 shaped as shown in FIG. 1 is devised in the present invention as inspired by a bee's stinger shaped as shown in FIG. 2.

With reference to FIG. 2, the photograph in a view on the upper right side of FIG. 2 is an enlarged photograph of the bee's stinger. When looked closely at the photograph, it may be seen that the bee's stinger has numerous wedge-shaped protrusions provided on the periphery of the main longitudinal direction. The reason why the bee's stinger is not easily pulled out at a point where the bee's stinger is inserted is because the wedge-shaped shape may strongly resist force applying in a direction where the bee's stinger is pulled out by being hung like a hook on the inner wall of the passage generated in the process of the insertion of the bee's stinger.

By simplifying a bee's stinger shape as shown in the view on the lower right side of FIG. 2, the shape of the microneedle according to the present invention may begin to emerge. Therefore, the microneedle 1 according to the present invention includes a body having a long length and side surface wedges provided on the outer circumferential surface of the body.

In addition, the side surface wedges may be provided to configure a plurality of layers so as to be more firmly prevented from being pulled back in a reverse direction, and each side surface wedge may be provided in a continuous shape over all or part of the outer circumferential surface of the body of the microneedle 1.

Meanwhile, one problem that may occur is that the effect of achieving the tight conjugation while minimizing pain and damage to the human body is achieved as above, but since the side surface wedge shape is an unusual three-dimensional shape, it may be wondered whether the process of realizing such a shape in members in sizes of the micrometer is complicated and costly.

In this regard, the production method of the microneedle array 30 according to the present invention may allow the production process of the microneedle array 30 according to the present invention to be completed in a few simple processes, thereby realizing a reduction in the production cost.

Figure 4:
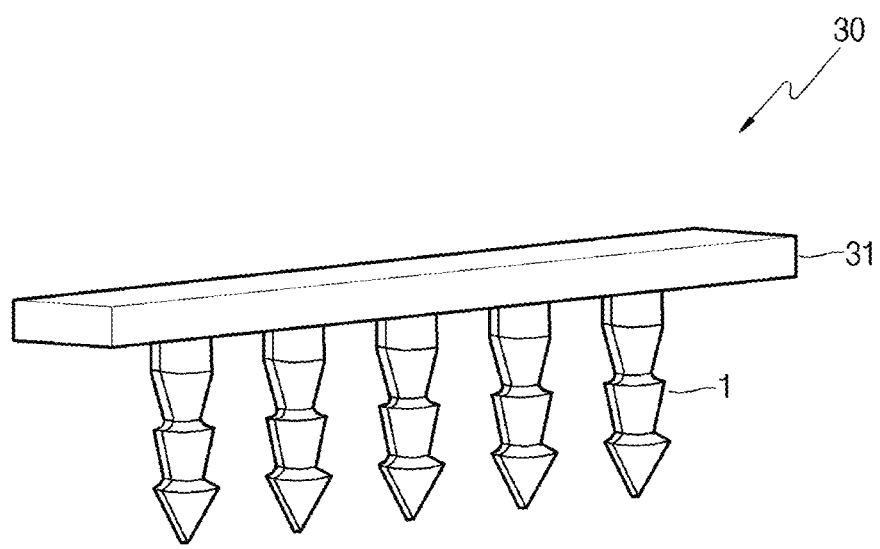
FIG. 4 is a perspective view of one microneedle array produced in FIGS. 3A and 3B.

For reference, because the microneedle 1 is produced in a subminiature size in a micrometer unit, it is difficult to suture an incision site using only one microneedle 1. Therefore, a plurality of microneedles is arranged long in a line as shown in FIG. 4 and is produced and used as a microneedle array 30 in which one end of each of all the microneedles 1 arranged in the line is connected to one base 31.

Figure 3A:
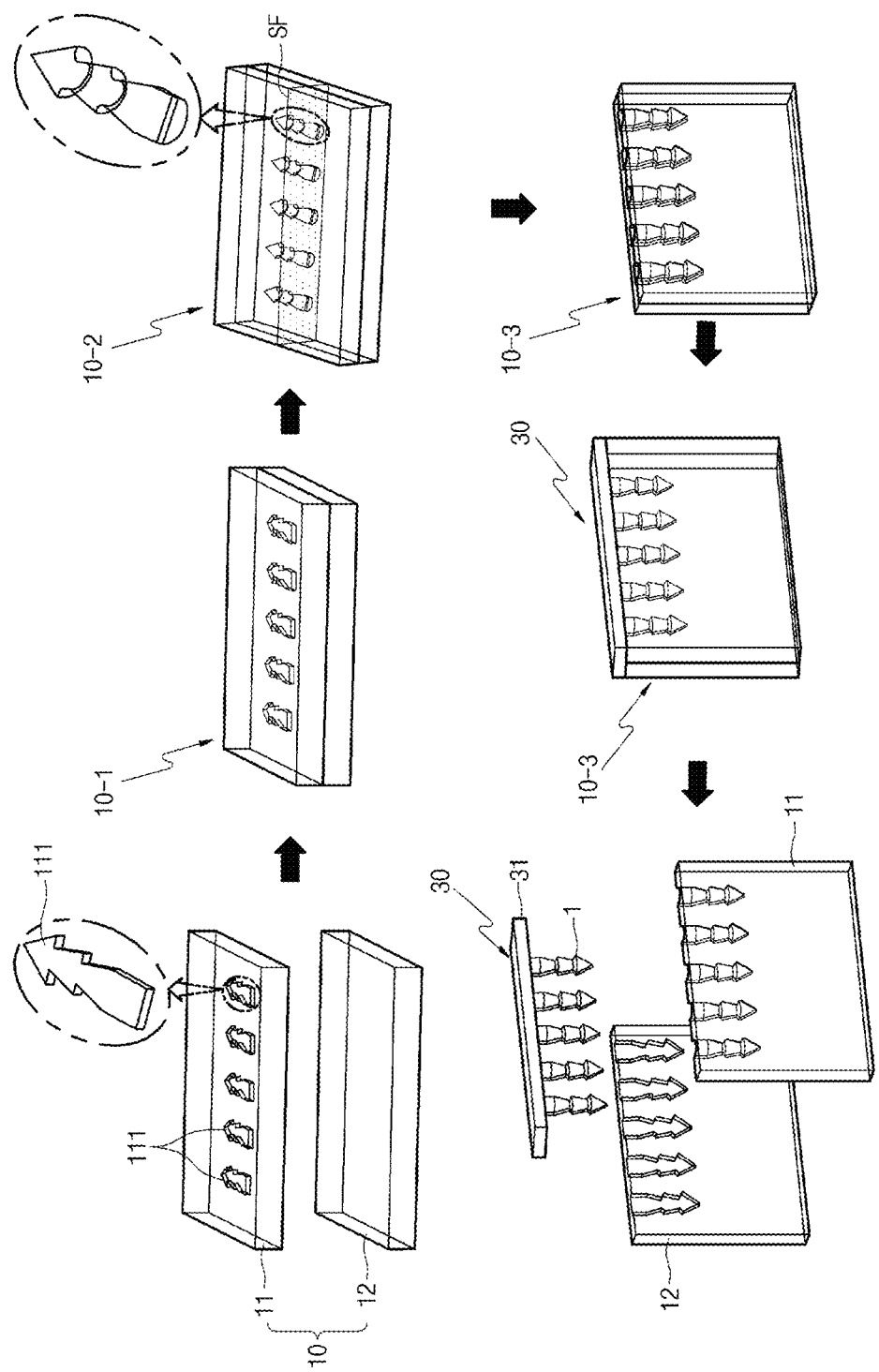
FIG. 3A shows a process flowchart illustrating a production method of a microneedle array using a mold for production of the microneedle array according to the present invention.

Specifically, as shown in FIG. 3A, the production method of the microneedle array 30 according to the present invention includes a step of producing a preliminary mold 10-1 provided with two-dimensional patterns 111, a step of producing a three-dimensional microneedle array mold 10-2, and a step of completing the microneedle array 30.

The step of producing the preliminary mold 10-1 is shown in a view on an upper left side of FIG. 3A. As the molds shown in FIG. 3A are molds for one microneedle array 30, a plurality of microneedles 1 is arranged in a line in parallel with each other in one mold. When Looked at one enlarged view which is for any one of mold shapes of the microneedle 1, the microneedle 1 in the view on the upper left side of FIG. 3A is provided in a two-dimensional planar shape.

However, the planar shape is produced in a form having a slight depth provided therein, the same as in a printing method of the patterns 111, in the production process. Therefore, even though expressed as the two-dimensional patterns 111, since the two-dimensional patterns 111 each have a predetermined thickness, a space in which a certain amount of air is held is provided as deep as each of the patterns 111 in reality.

More specifically, the preliminary mold 10-1 is provided by bonding a first plate member 11 and a second plate member 12 to each other, as shown in the view on the upper left side of FIG. 3A. That is, the two-dimensional patterns 111 is printed on one surface of opposite surfaces, the one surface bonded to the second plate member 12, and then the first plate member 11 and the second plate member 12 are bonded to each other to provide the preliminary mold 10-1. Here, the preliminary mold 10-1 is provided with a shape of the two-dimensional microneedle array 30 having a predetermined thickness therein. At this time, in the process of bonding the first plate member 11 and the second plate member 12, a predetermined amount of air is filled inside the shape of the two-dimensional microneedle array 30.

When heat is applied to the preliminary mold 10-1 provided as above or air is injected in a form of an injection thereto, the air inside the patterns 111 having the shape of the two-dimensional microneedle 1 expands and then the two-dimensional shape expands into a three-dimensional shape as indicated by an enlarged view on an upper right side of FIG. 3A. In particular, the method of applying heat is more efficient because no equipment for injecting air is required.

Figure 3B:
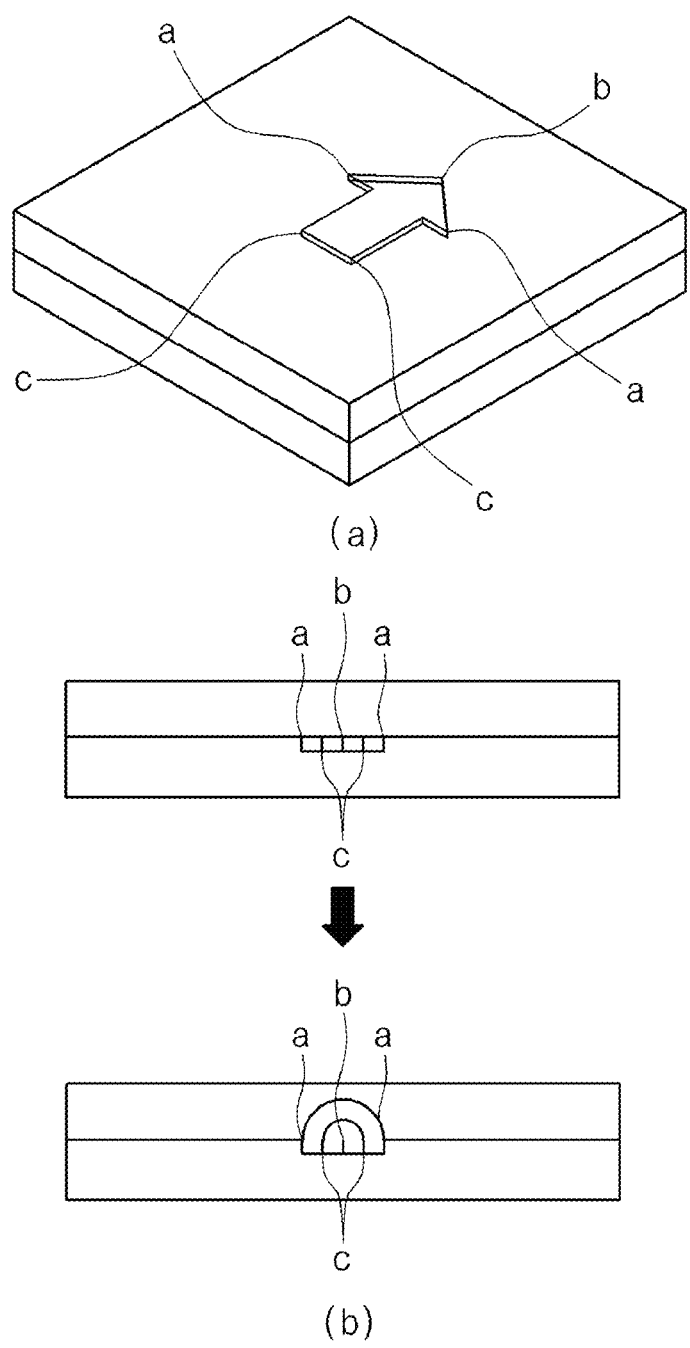
FIG. 3B shows conceptual views illustrating a key principle of the production method in FIG. 3A.

A three-dimensionalization process of the two-dimensional patterns 111 through the above-mentioned heating is conceptually shown using an arrow shape in FIG. 3B. With reference to a view (a) in FIG. 3B, the arrow shape provided in the two-dimensional shape is located between the two plate members due to the bonding of the two plate members.

At this time, when heat is applied to the plate member shown in the view (a) in FIG. 3B, a process shown in views (b) in FIG. 3B occurs. In this case, when the microneedle array mold 10-2, which is provided after the pattern shape inside the mold is three-dimensionally deformed by applying heat to the preliminary mold 10-1, is cured, the microneedle array mold 10-3 as shown in a view on a lower right side of FIG. 3A is completed.

In addition, the step of producing the preliminary mold 10-1 may further include a step of preparing a master mold (not shown) providing the microneedle patterns 111 having a two-dimensional shape in the master mold (not shown) by preparing a master mold (not shown) before a step of preparing the first plate member 11, wherein, in the step of preparing the first plate member 11, the microneedle patterns 111 having the two-dimensional shape are provided on the first plate member 11 in a manner of replicating the master mold. (Not shown)

Here, the master mold is made of silicon material, and in the step of preparing the master mold, the microneedle patterns 111 having the two-dimensional shape may be provided on the prepared master mold by a photolithography process.

Expansion of the microneedle patterns 111 having the two-dimensional shape may occur in various forms. However, in particular, when viewed with reference to the views (b) in FIG. 3B, the plate member provided with the two-dimensional patterns 111 may be produced in a state where curing is performed over an entire portion thereof, and the remaining plate member, which is the plate member not provided with the two-dimensional patterns 111, may be produced in a state where curing is performed for a portion except a surface in contact with the patterns 111, wherein curing is not performed for the surface in contact with the patterns 111. Accordingly, when the air inside the patterns 111 is expanded by applying the heat to the plate member, the air expands to a soft portion where the pattern 111 is not provided. In addition, the form of expansion expands in a semicircle shape because the air pressure is uniformly applied in all directions as shown in views (b) in FIG. 3B.

In addition, the semicircle shape becomes a shape which is a three-dimensional semicircle expanded from the two-dimensional shape. That is, in FIG. 3B, when the head part of the arrow surrounded by two "a" points and one "b" point is inflated, it becomes a shape corresponding to half of a cone, and a part except the head part of the arrow corresponds to half of a cylindrical shape.

Therefore, when looking FIG. 3A again with reference to FIG. 3B, it may be seen that in the enlarged view on the upper right side of FIG. 3A, the pattern 111 having the shape of the microneedle 1 expands in a semicircular shape toward the bottom.

In this manner, the shape of the microneedle 1 expands, thereby providing a three-dimensional shape, and then treatment is performed to cure a periphery of the three-dimensional shape. Then, the mold is cut along a virtual surface SF passing through a region of the base 31 of all the microneedles 1, that is, the virtual surface SF simultaneously passing through a region of an opposite end side of each sharp peak of the microneedle 1, whereby the microneedle array mold 10-3 is finally completed as shown in the view on the lower right side of FIG. 3A.

Subsequently, the biocompatible and biodegradable liquid is poured into one finished microneedle array mold 10-3 and the microneedle array mold 10-3 is removed after the liquid is solidified. Then, as shown in a view on the lower left side of FIG. 3A, the production of one microneedle array 30 is completed. One microneedle array 30 completed in this manner is shown in FIG. 4.

In particular, in this case, the liquid may be a silk fibroin material but is not limited thereto. After pouring the liquid into the microneedle array mold 10-3, the microneedle array mold 10-3 is put into a vacuum chamber (not shown), thereby allowing the bubbles that may be present in the liquid to be removed.

At this time, for reference, in order to allow the shape of the side surface wedges not to be damaged in the process of separation of the microneedle array 30 from the microneedle array mold 10-3, the microneedle array mold 10-3 may be decomposed in the separation process.

For the forms of decomposition, the microneedle array mold 10-3 may be decomposed into two parts as in FIG. 3A or may be decomposed into several more pieces. In addition, the microneedle array mold 10-3 may be maintained in a somewhat flexible state so that the microneedle array 30 may be more flexibly separated from the microneedle array mold 10-3.

Figure 9A:
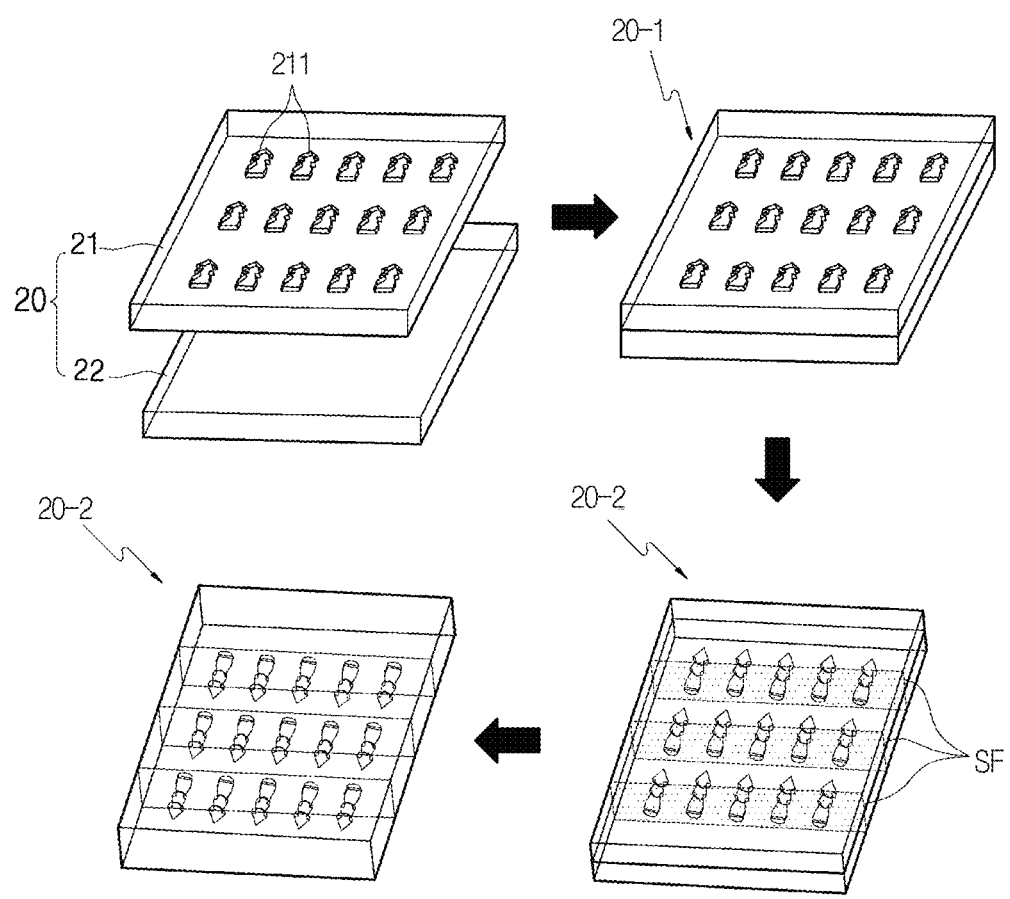
FIGS. 9A and 9B are process flowcharts of production of a plurality of microneedle arrays.

When a plurality of microneedle arrays 30 is allowed to be produced at a time rather than the microneedle array 30 is produced one by one as shown in FIG. 3A, the microneedle array 30 may be supplied more cheaply by significantly enhancing the production efficiency. A process of producing the plurality of microneedle arrays 30 mentioned above is shown in FIGS. 9A and 9B.

The process of producing the plurality of microneedle arrays 30 is mostly the same as the process of producing a single of the microneedle array 30 described above. However, one difference is that incision surfaces are formed in a plurality of places as shown in a view on a lower right side of FIG. 9A.

Figure 9B:
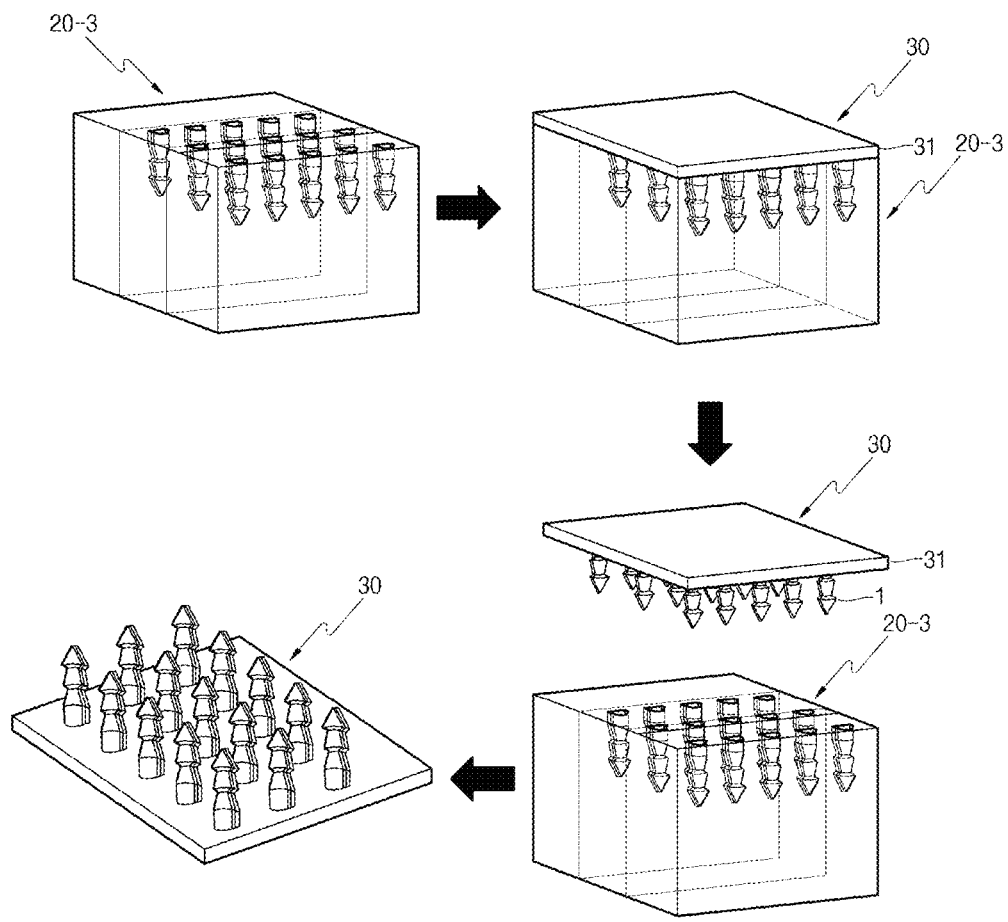

Each of the plurality of microneedle array molds 20-2 thus cut out is disposed in a state where a pointed portion of the microneedle 1 faces downward and an end portion having a large cross section of the microneedle 1 faces upward, as shown in a view on the upper left of FIG. 9B.

That is, each microneedle array mold 20-2 is rearranged in a form so that, when the casting is put thereinto, the casting may not flow out again. This process is a different aspect from the production process of a single microneedle array 30. The subsequent process is the same as the production process of any one microneedle array 30 as described above.

In other words, in a step of producing the preliminary mold 20-1, any one of microneedle arrays 30 is arranged in a form, in which microneedles 1 are each arranged in one line and each have longitudinal directions all facing the same direction, and a plurality of microneedle arrays 30 is provided, wherein the plurality of microneedle arrays 30 is arranged in parallel with each other.

Therefore, a step of producing the microneedle array mold 20-2 may further include, after a hollow space having the three-dimensional shape of the microneedle 1 is provided as the preliminary mold (10-1 or 20-1) is heated, a step of opening the end portions of all of the microneedles 1 by cutting an end region of the base 31 side of the microneedles 1, arranged in one line for each microneedle array 30, along the virtual surface SF simultaneously passing through the end region of the base 31 side of the microneedles 1; and a step of completing the microneedle array mold 20-3 in which a plurality of microneedle arrays 30 is arranged in parallel with each other, by gathering all blocks of the microneedle array molds 20-2 provided by being cut along the virtual surface SF and then bonding all of the blocks to be in parallel with each other in a state where open end portions of all of the microneedles 1 face upward.

Figure 5:
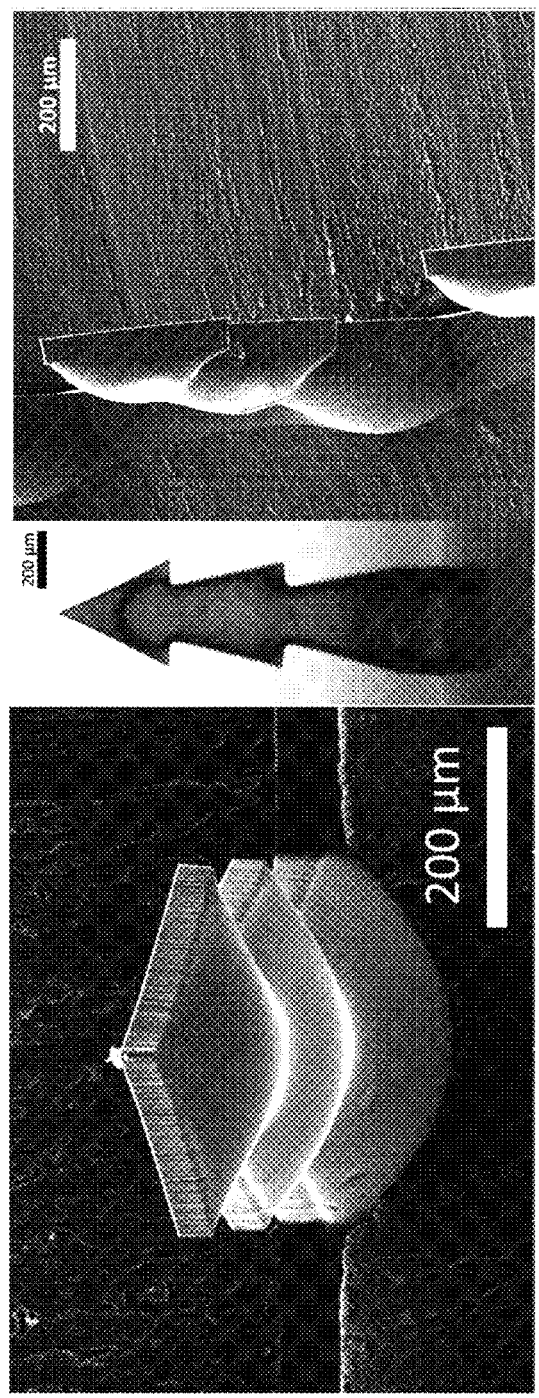
FIG. 5 shows photographs of a microneedle actually produced.
Figure 6:
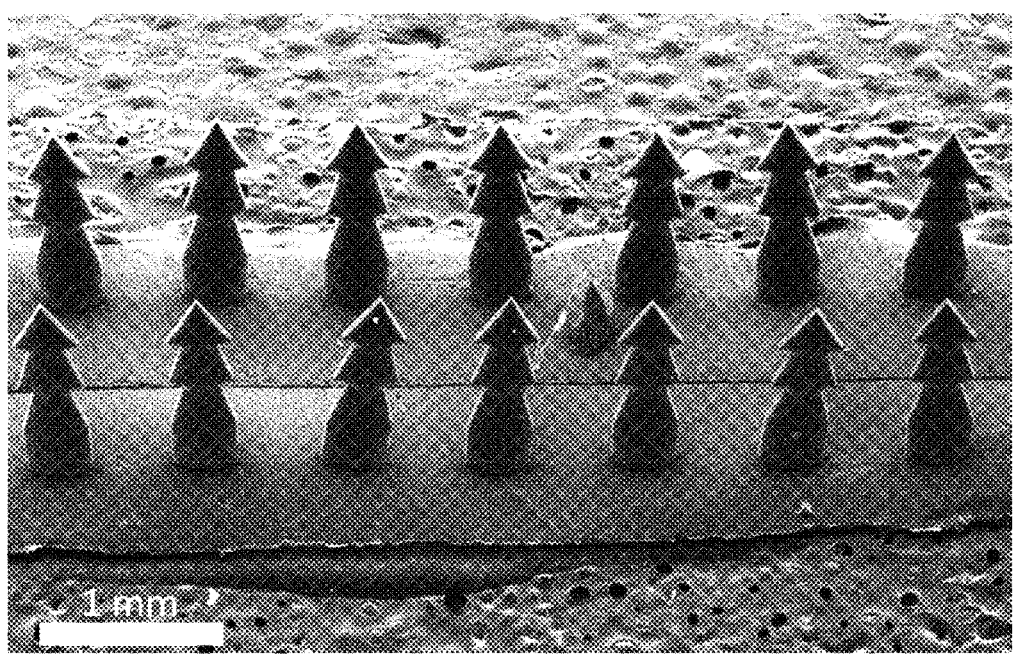
FIG. 6 is a photograph of a microneedle array actually produced.

Each microneedle 1 constituting the microneedle array 30 produced in this way is shown in the photographs in FIG. 5, and a photograph of two completed microneedle arrays 30 is shown in FIG. 6.

With reference to the photographs in FIG. 5, as described earlier, the microneedle 1 has a shape whose one surface expands in a semicircle toward a certain direction. In addition, the size is shown by way of an example in the photographs in FIG. 5, but is not necessarily limited thereto, and provided the bonding efficiency is maintained without applying pain to the affected area, the size may be made somewhat smaller or larger.

When a minimum force is required in a process of inserting, and a maximum force is required in a process of breaking away again, the performance of the microneedle 1 may have a good suture ability while minimizing pain.

Figure 7:
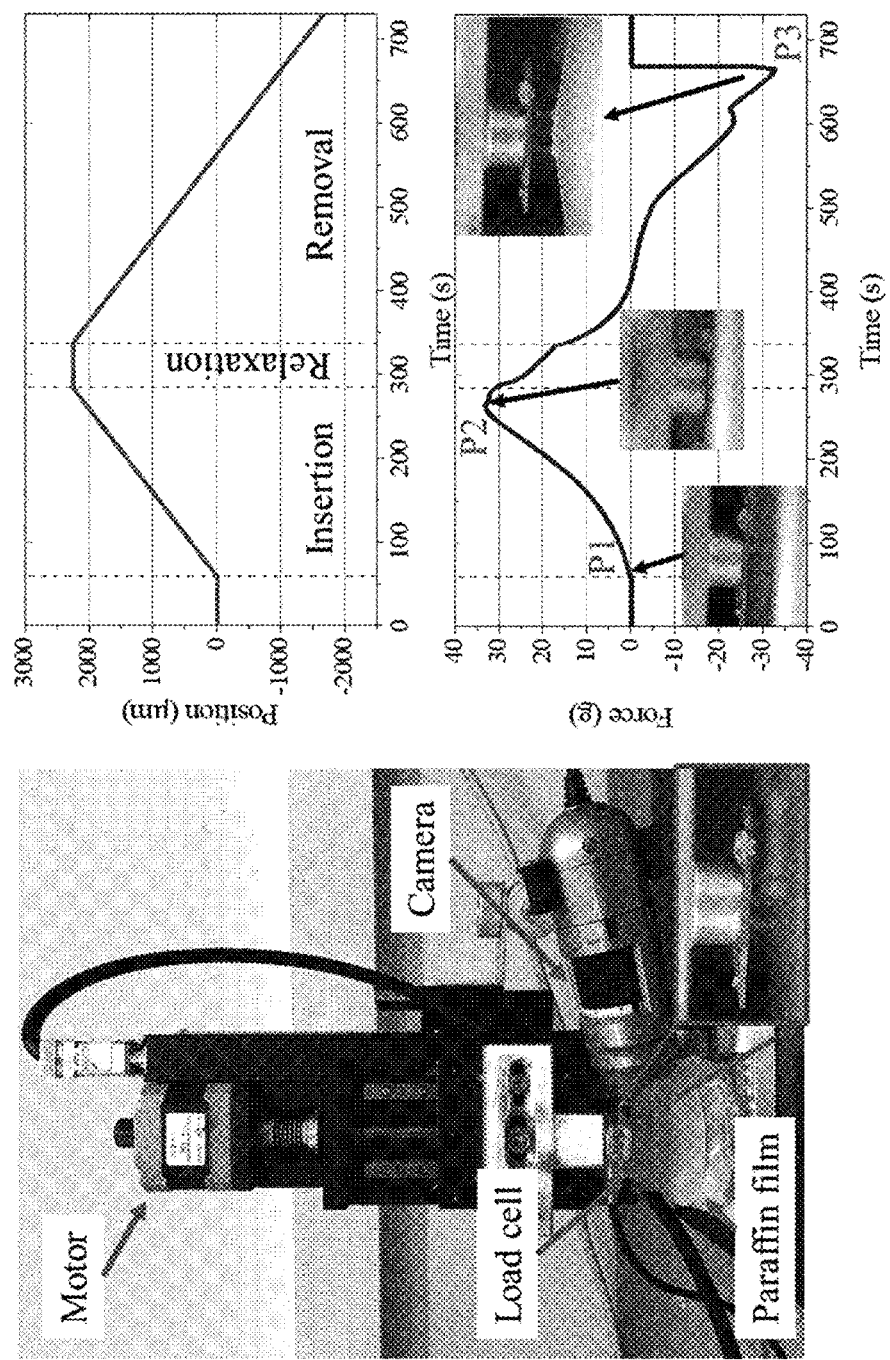
FIG. 7 shows a photograph illustrating a performance test equipment and graphs illustrating test results of the microneedle of FIG. 5.

As shown in the photograph in FIG. 7, an insert to replace the human body is paraffin having a texture and physical properties similar to those of the human body. Here, a motor installed in an experimental equipment operates a load cell to insert the microneedle 1 into the paraffin in a vertical direction.

A table shown in FIG. 8 illustrates comparison of the results of the experiments described above with respect to the conventional bell-shaped microneedle 1 and microneedles having other shapes.

With reference to the table of FIG. 8, the greater the retraction force is, the better the suture ability is, so that the bee's stinger has the most excellent suture ability. That is, the bee's stinger requires the largest force for the retreat, and the microneedle 1 according to the present invention is followed. The items listed on the far right column in the table of FIG. 8 are for the microneedle 1 according to the present invention.

For reference, any kind of material may be adopted as the material for the microneedle array 30 in the present invention as long as the material has biocompatibility and biodegradability and has a predetermined rigidity and elasticity as required for the microneedle 1. Even though w silk fibroin was used in the actual production experiment of the present invention, the material of the microneedle array 30 according to the present invention is not necessarily limited thereto.

The present invention described above is not limited to the above-described embodiments and the accompanying drawings. In addition, it will be evident to those who have ordinary knowledge in the art the present invention pertains that various substitutions, modifications, and changes are possible within the scope without departing from the technical spirit of the present invention.

What is claimed is:

1. A production method of a microneedle array, the microneedle array composed of a base and a plurality of microneedles arranged on a surface of the base, the microneedle including a needle-shaped body protruded from the base and barb or wedge shapes each provided in an acute angle toward the base along a circumference of the body, the method comprising:
    producing preliminary molds provided with two-dimensional patterns having a shape of the microneedle array therein;
    producing microneedle array molds having a three-dimensional shape by expanding air inside the patterns to plastically deform the preliminary molds and thereby deform the patterns into a cast form having the three-dimensional shape; and
    after pouring a biodegradable resin into the microneedle array molds and solidifying the biodegradable resin, completing the microneedle array by removing the microneedle array molds.

2. The method of claim 1, wherein,
    in the producing the preliminary mold, the patterns having the two-dimensional shape are produced to have a predetermined thickness, thereby allowing the air to be contained inside the patterns having the two-dimensional shape; and
    in the producing the microneedle array molds, the air inside the patterns having the two-dimensional shape expands as the preliminary mold is heated, thereby allowing the two-dimensional patterns to be deformed into the three-dimensional shape.

3. The method of claim 1, wherein the producing the preliminary mold further includes:
    preparing a first plate member providing the microneedle patterns having the two-dimensional shape having a predetermined depth on one surface of the first plate member;
    preparing a second plate member; and
    completing the preliminary mold by bonding the first plate member and the second plate member to each other.

4. The method of claim 3, wherein,
    in the producing the preliminary mold, the first plate member allows the microneedle patterns having the two-dimensional shape to be provided and then cured, and the second plate member allows a remaining portion except for a portion in contact with the microneedle patterns to be cured, whereby a certain amount of the air is allowed to exist in the microneedle patterns in contact with the bonding surface between the first plate member and the second plate member; and
    in the producing the microneedle array molds, when the preliminary mold is heated, the air existing in the microneedle patterns expands toward the second plate member, whereby a hollow space having a three-dimensional shape is allowed to be provided.

5. The method of claim 4, wherein the producing the preliminary molds further includes preparing a master mold providing the microneedle patterns having the two-dimensional shape in the master mold by preparing the master mold prior to the preparing the first plate member, wherein, in the preparing the first plate members, the microneedle patterns having the two-dimensional shape are provided on the first plate member in a manner of replicating the master mold.

6. The method of claim 5, wherein, the master mold is made of silicon material, and in the preparing the master mold, the microneedle patterns having the two-dimensional shape are provided on the prepared master mold by a photolithography process.

7. The method of claim 4, wherein,
in the producing the preliminary mold, any one of microneedle arrays is arranged in a form, in which microneedles are each arranged in one line and each have longitudinal directions all facing the same direction, and a plurality of microneedle arrays is provided, wherein the plurality of microneedle arrays is arranged in parallel with each other; and
the producing the microneedle array molds further includes,
after the hollow space having the three-dimensional shape of the microneedle is provided as the preliminary mold is heated, opening the end portions of the microneedles by cutting an end region of the base side of the microneedles, arranged in one line for each microneedle array, along the virtual surface simultaneously passing through the end region of the base side of the microneedles, and
completing the microneedle array mold in which a plurality of microneedle arrays is arranged in parallel with each other, by gathering all blocks of the microneedle array molds provided by being cut along the virtual surface and then bonding the blocks to be in parallel with each other in a state where open end portions of all of the microneedles face upward.

8. The method of claim 3, wherein,
in the producing the preliminary mold, the first plate member allows the microneedle patterns having the two-dimensional shape to be provided and then cured, and the second plate member allows a remaining portion except for a portion in contact with the microneedle patterns to be cured, whereby a certain amount of the air is allowed to exist in the microneedle patterns in contact with the bonding surface between the first plate member and the second plate member; and
in the producing the microneedle array molds, when the preliminary mold is heated, the air existing in the microneedle patterns expands toward the second plate member, whereby a hollow space having a three-dimensional shape is allowed to be provided.

9. The method of claim 8, wherein the producing the preliminary molds further includes preparing a master mold providing the microneedle patterns having the two-dimensional shape in the master mold by preparing the master mold prior to the preparing the first plate member, wherein, in the preparing the first plate members, the microneedle patterns having the two-dimensional shape are provided on the first plate member in a manner of replicating the master mold.

10. The method of claim 9, wherein, the master mold is made of silicon material, and in the preparing the master mold, the microneedle patterns having the two-dimensional shape are provided on the prepared master mold by a photolithography process.

11. The method of claim 8, wherein,
in the producing the preliminary mold, any one of microneedle arrays is arranged in a form, in which microneedles are each arranged in one line and each have longitudinal directions all facing the same direction, and a plurality of microneedle arrays is provided, wherein the plurality of microneedle arrays is arranged in parallel with each other; and
the producing the microneedle array molds further includes,
after the hollow space having the three-dimensional shape of the microneedle is provided as the preliminary mold is heated, opening the end portions of the microneedles by cutting an end region of the base side of the microneedles, arranged in one line for each microneedle array, along the virtual surface simultaneously passing through the end region of the base side of the microneedles, and
completing the microneedle array mold in which a plurality of microneedle arrays is arranged in parallel with each other, by gathering all blocks of the microneedle array molds provided by being cut along the virtual surface and then bonding the blocks to be in parallel with each other in a state where open end portions of all of the microneedles face upward.

* * * * *